US00PP21146P3

(12) United States Plant Patent
Bos

(10) Patent No.: US PP21,146 P3
(45) Date of Patent: Jul. 6, 2010

(54) ***CARYOPTERIS* PLANT NAMED 'WHITE SURPRISE'**

(50) Latin Name: *Caryopteris clandonensis*
Varietal Denomination: White Surprise

(76) Inventor: Jan Jacob Bos, Voordersteeg 26, 7384 AG Wilp (NL)

( * ) Notice: Subject to any disclaimer, the term of this patent is extended or adjusted under 35 U.S.C. 154(b) by 0 days.

(21) Appl. No.: 12/386,381

(22) Filed: Apr. 17, 2009

(65) Prior Publication Data

US 2009/0210985 P1 Aug. 20, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Upov Plant Variety Database 2009/06 search for cultivar White Surprise. p. 1.*

* cited by examiner

*Primary Examiner*—Annette H Para

(57) ABSTRACT

A new and distinct cultivar of *Caryopteris* plant named 'WHITE SURPRISE' that is characterized by broad upright habit, large white variegated leaves, and violet-blue flowers. In combination these traits set 'WHITE SURPRISE' apart from all other existing varieties of *Caryopteris* known to the inventor.

2 Drawing Sheets

Genus: *CARYOPTERIS.*
Species: *clandonensis.*
Denomination: 'WHITE SURPRISE'.

BACKGROUND OF THE INVENTION

The present invention relates to a new variety of blue mist, a perennial shrub grown for use as a specimen plant, for borders, and the landscape. The new invention from the family Verbenaceae is known botanically as *Caryopteris clandonensis* and will be referred to hereinafter by the cultivar name 'WHITE SURPRISE'.

'WHITE SURPRISE' was discovered in June 2005 as a branch sport of *Caryopteris clandonensis* 'Heavenly Blue' (unpatented). The inventor discovered 'WHITE SURPRISE' at the inventor's nursery in Wilp, The Netherlands growing in a commercial crop of 'Heavenly Blue'. The parent of 'WHITE SURPRISE' is an individual *Caryopteris clandonensis* 'Heavenly Blue'.

'WHITE SURPRISE' exhibits broad upright habit, aromatic stems and foliage, large white variegated leaves, and violet-blue flowers. 'WHITE SURPRISE' grows to 55 cm. in height and 80 cm. in width at maturity. 'WHITE SURPRISE' exhibits its distinguishing characteristics to best effect when grown in full sun or light shade, with moderate water. 'WHITE SURPRISE' grows well in most soil types. Susceptibility to pests is similar to the species, however, there are no particular diseases known to the inventor which affect 'WHITE SURPRISE'. 'WHITE-SURPRISE' is hardy at least in USDA Zone 6.

The closest comparison plant known to the inventor is the parent variety, *Caryopteris clandonensis* 'Heavenly Blue'. 'WHITE SURPRISE' is distinguishable from the comparison plant by white variegated leaves.

The first asexual reproduction of 'WHITE SURPRISE' was conducted by the inventor, at the inventor's nursery in August 2005. The method used was vegetative cuttings and the location was Wilp, The Netherlands. Since that time under careful observation 'WHITE SURPRISE' has been determined fixed, stable and to reproduce true to type in subsequent generations of asexual propagation.

The inventor filed an application for European Community Plant Breeders' Rights for 'WHITE SURPRISE' on Apr. 30, 2007, Ser. No. 2007/0834. At the time of filing the application for European Community Plant Breeder' Right cited above, and until June 2008, all plants of 'WHITE SURPRISE' remained at the inventor's nursery under the inventor's control. The first public distribution of any plants of 'WHITE SURPRISE' took place in June 2008 when the Inventor commenced deliveries of his first plants to garden centers in Boskoop, The Netherlands.

SUMMARY OF THE INVENTION

The following traits have been repeatedly observed and represent the distinguishing characteristics of the new *Caryopteris* cultivar named 'WHITE SURPRISE'. These traits in combination distinguish 'WHITE SURPRISE' from all other existing varieties of *Caryopteris* known to the inventor. 'WHITE SURPRISE' has not been tested under all possible conditions. Phenotypic differences may be observed with variations in environmental, climatic, and cultural conditions without however any variance in genotype.

1. 'WHITE SURPRISE' exhibits broad upright habit.
2. 'WHITE SURPRISE' exhibits large white variegated leaves.
3. 'WHITE SURPRISE' exhibits violet-blue flowers.
4. 'WHITE SURPRISE' exhibits aromatic stems and foliage.
5. 'WHITE SURPRISE' reaches 55 cm. in height and 80 cm. in width at maturity.
6. 'WHITE SURPRISE' is hardy at least in USDA Zone 6.

BRIEF DESCRIPTION OF THE DRAWINGS

The accompanying color drawings illustrate the overall appearance of the new *Caryopteris* cultivar named 'WHITE SURPRISE' showing color as true as is reasonably possible to obtain in color reproductions of this type. The drawings were made from a 4-year-old plant which had been grown out-of-doors in Wilp, The Netherlands in 7.5-liter containers. Color in the drawings may differ from color values cited in the detailed botanical description, which accurately describe the actual color of 'WHITE SURPRISE'.

The drawing labeled

The drawing labeled

Figure 1:
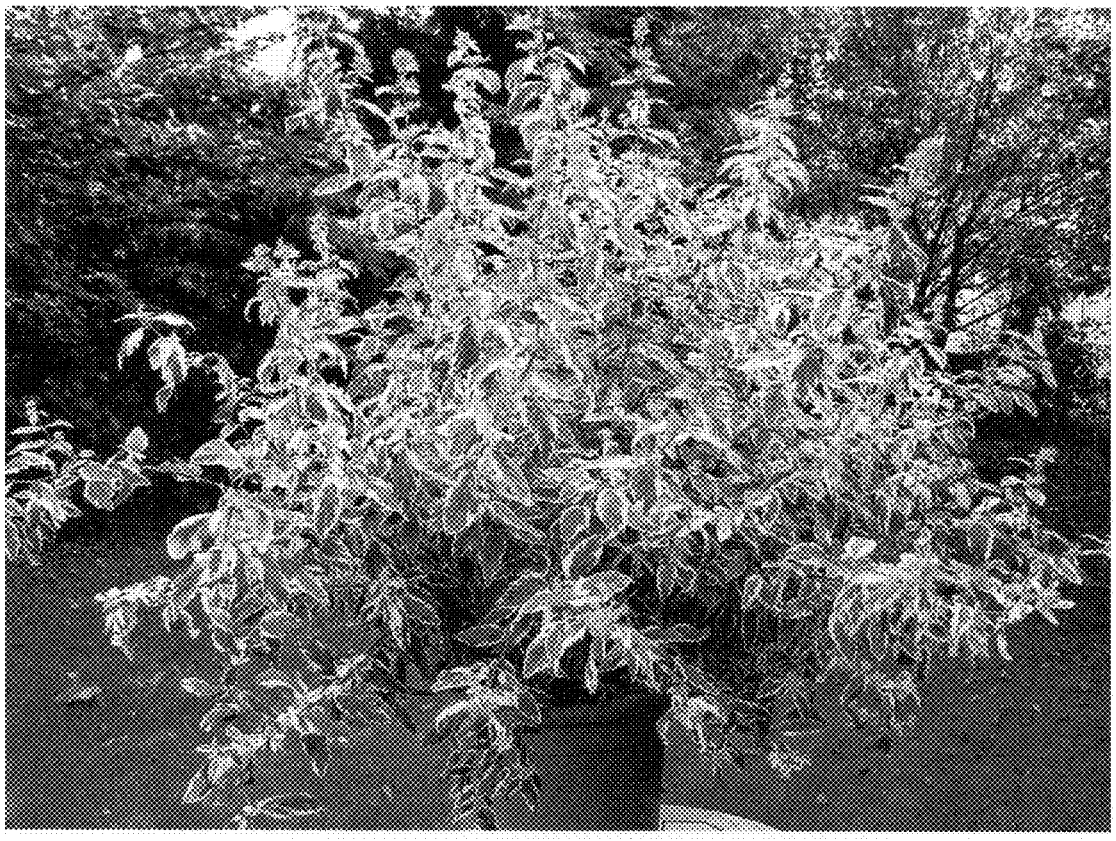
FIG. 1 depicts a side view of a plant of 'WHITE SURPRISE' illustrating habit, foliage, and flower color.
Figure 2:
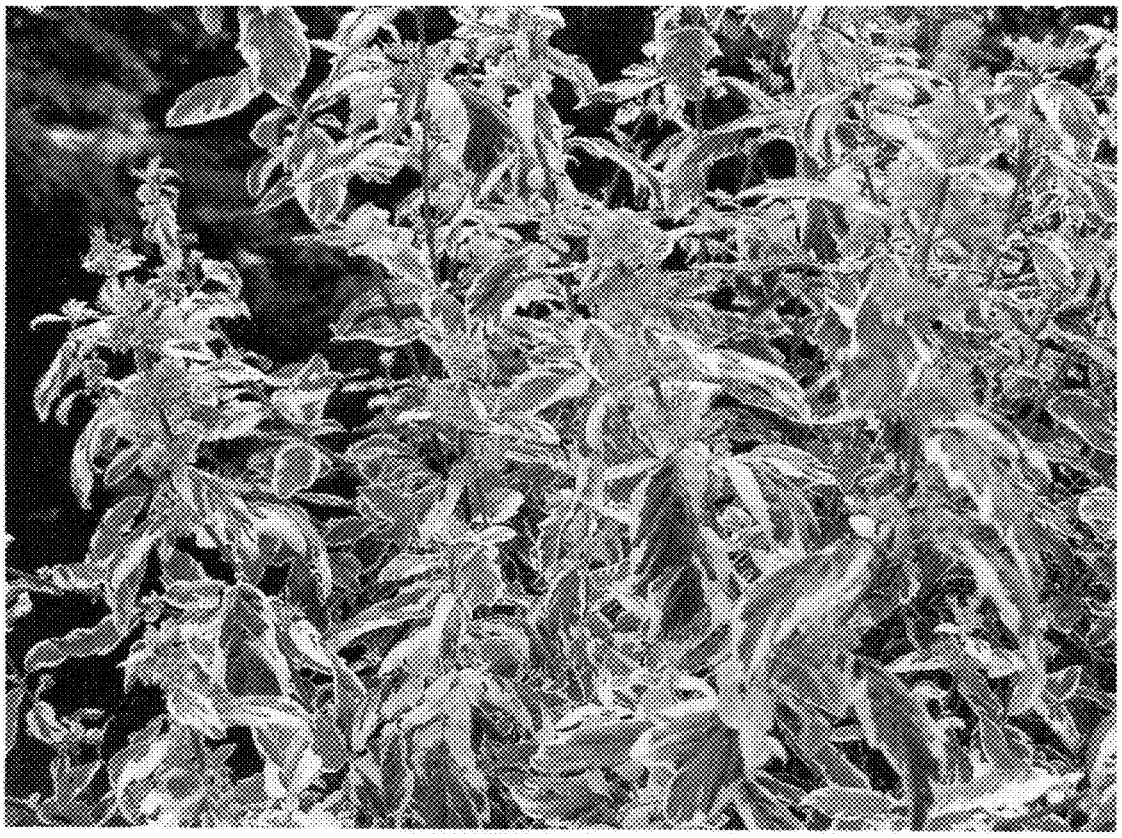
FIG. 2 depicts a close-up view illustrating inflorescence and foliage.

Both drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Caryopteris* cultivar named 'WHITE SURPRISE'. Observations, measurements, values and comparisons were collected in October from plants grown out-of-doors in Wilp, The Netherlands. Plants in the drawings are 4-years-old and in 7.5-liter containers. The range of daytime temperatures was 12° Centigrade to 25° Centigrade, and the range of night temperatures was 3° Centigrade to 14° Centigrade. Light level was normal outdoor light. No growth retardant or photoperiodic treatment was used. Color determinations are made in accordance with The 2001 Royal Horticultural Society Colour Chart from London, England, except where general color terms of ordinary dictionary significance are used. The growing requirements of the new variety 'WHITE SURPRISE' are similar to the species.

Botanical classification: *Caryopteris clandonensis* 'WHITE SURPRISE'.

Family: Verbenaceae.

Genus: *CARYOPTERIS.*

Species: *clandonensis.*

Denomination: 'WHITE SURPRISE'.

Common name: Blue mist.

Habit: Broad upright.

Shape: Globular.

Commercial category: Perennial shrub.

Use: Border, specimen, and landscape.

Suggested commercial container size: 1.3-liter container and larger.

Parentage: The new variety *Caryopteris clandonensis* 'WHITE SURPRISE' was discovered as a branch sport of the following:

*Parent.*—An individual *Caryopteris clandonensis* 'Heavenly Blue' (unpatented).

Propagation method: Vegetative cuttings.

Rooting system: Fine.

Vigor (range): Moderate.

Growth rate: Moderate.

Crop time (average): 22 months to produce a 1.3-liter container from stem cuttings.

Mature height (average): 55 cm.

Mature width (average): 80 cm.

Cultural requirements: Performs best in full sun, with moderate water, and most soil types.

Pest susceptibility: Same as species.

Disease susceptibility: None known to the inventor.

Hardiness: Hardy at least in USDA Zone 6.

Special growing recommendations: Pinch to improve branching.

Stem:

*Branching habit.*—Basal and free lateral branching.

*Lateral branch quantity* (*average*).—112 in number.

*Shape.*—Cylindrical.

*Surface.*—Pubescent.

*Pubescence color.*—157A.

*Stem appearance.*—Semi-glossy.

*Color.*—145A, 199C, and N199A are all individually present.

*Stem length* (*average*).—12.3 cm.

*Stem diameter* (*average*).—2 mm.

*Stem strength.*—Moderately strong.

*Internode* (*average*).—3.1 cm.

*Stem fragrance.*—Pleasantly aromatic.

Foliage:

*Type.*—Deciduous.

*Leaf arrangement.*—Opposite.

*Leaf division.*—Simple.

*Leaf quantity* (*average*).—8 per lateral stem.

*Leaf margin* (*range*).—Coarsely to irregular serrate.

*Leaf surface* (*abaxial*).—Densely pubescent.

*Pubescence color.*—157A.

*Leaf surface* (*adaxial*).—Glabrous.

*Leaf texture.*—Rugose.

*Leaf shape.*—Ovate and moderately convex.

*Leaf length* (*average*).—6.4 cm.

*Leaf width* (*average*).—2.8 cm.

*Young leaf color* (*abaxial surface*).—191C, 191D and 155A are all individually present.

*Young leaf color* (*adaxial surface*).—137B and 150D both present.

*Mature leaf color* (*abaxial surface*).—190B, 190C, 150D and 155A are all individually present.

*Mature leaf color* (*adaxial surface*).—137A, 150D and 155A.

*Leaf apex.*—Acute.

*Leaf base.*—Rounded.

*Venation pattern.*—Pinnate.

*Vein color* (*abaxial surface*).—145B and 145C.

*Vein color* (*adaxial surface*).—145A.

*Attachment.*—Petiolate.

*Petiole surface.*—Puberulent.

*Petiole color.*—145A and 145B.

*Petiole dimensions* (*average*).—1.1 cm. in length and 1.2 mm. in diameter.

*Durability of foliage to stress.*—Moderate.

*Tendrils and stipules.*—None observed.

*Leaf fragrance.*—Pleasantly aromatic.

Inflorescence:

*Type.*—Thyrse.

*Arrangement.*—Terminal and axillary.

*Inflorescence.*—Dimensions (average): 2.3 cm. in length and 2.5 cm in width.

*Rate of opening* (*range*).—40% of inflorescence opens in 10 days; complete after 3 weeks.

*Blooming months.*—September and October.

*Flower quantity* (*average*).—32 per inflorescence.

*Flower quantity* (*average*).—16 per lateral stem.

*Bud quantity* (*average*).—16 per lateral stem.
*Flower quantity per plant* (*average*).—>3000.
*Flower aspect.*—Upright to moderately outward.
*Flower type.*—Single.
*Persistent or self-cleaning.*—Self-cleaning.
*Peduncle shape.*—Cylindrical.
*Peduncle surface.*—Puberulent.
*Peduncle strength.*—Moderate.
*Peduncle color.*—144B.
*Peduncle dimensions* (*average*).—9 mm. in length and 1 mm. in diameter.
*Terminal peduncle angle.*—0°.
*Axillary peduncle angle.*—30°.
*Pedicel dimensions.*—2 mm. in length and 0.75 mm. in diameter.
*Pedicel color.*—144B.
*Pedicel angle.*—10°.
*Pedicel strength.*—Moderate.
*Bud quantity* (*average*).—32 per inflorescence.
*Bud shape.*—Obovate.
*Bud apex.*—Rounded.
*Bud color.*—N88D and 91B.
*Rate of opening.*—3 days to open.
*Bud surface.*—Pubescent.
*Bud dimensions.*—5 mm. in length and 2 mm. in diameter.
*Corolla shape.*—Campanulate and 5-lobed.
*Corolla color when opening* (*dorsal surface*).—92A and N88C.
*Corolla color when opening* (*ventral surface*).—92A.
*Corolla color fades to.*—92C.
*Corolla dimensions.*—1.1 cm. in depth and 5 mm. in diameter.
*Corolla surface* (*ventral and dorsal*).—Glabrous.
*Corolla longevity on plant* (*average*).—12 days.
*Lobes.*—5 in number.
*Lobe arrangement.*—Rotate, fused into campanulate shape/lower lobe longer than other 4 lobes.
*Lobe length* (*average*).—7 mm./lower lobe 1.0 cm.
*Lobe width* (*average*).—1.5 mm./lower lobe 4 mm.
*Lobes fused or unfused.*—Fused.
*Fully opened lobe color* (*ventral surface*).—92B.
*Fully opened lobe color* (*dorsal surface*).—92B and N88D.
*Lobe color fades to.*—92C.
*Lobe margin.*—Entire/margin of lower lobe laciniate.
*Lobe shape.*—Obovate lower lobe spathulate.
*Lobe surface* (*abaxial and adaxial*).—Glabrous.
*Lobe apex.*—Obtuse lower lobe laciniate.
*Calyx shape.*—Campanulate.
*Calyx color* (*immature*).—193B.
*Calyx dimensions.*—4 mm. in length and 3 mm. in width.
*Sepals.*—5 in number.
*Sepal shape.*—Narrow elliptic.
*Sepal dimensions.*—4 mm. in length and 1 mm. in width.
*Sepals fused or unfused.*—Fused.
*Immature sepal color* (*dorsal surface*).—193B.
*Immature sepal color* (*ventral surface*).—144D.
*Mature sepal color* (*ventral surface*).—144D.
*Mature sepal color* (*dorsal surface*).—144D and 126A.
*Sepal margin.*—Entire.
*Sepal apex.*—Acute.
*Sepal surface* (*ventral and dorsal*).—Glabrous.
*Flower fragrance.*—None observed.

Reproductive organs:
*Stamen quantity.*—4 in number.
*Stamen length.*—5.5 mm.
*Stamen color.*—97B and 97C.
*Anther color.*—116A.
*Anther shape.*—Oblong and dorsifixed.
*Anther length* (*average*).—0.5 mm.
*Pollen amount.*—Minimal.
*Pollen color.*—161C.
*Pistil quantity* (*average*).—1 in number.
*Pistil length* (*average*).—1 cm.
*Pistil color.*—N88D.
*Style length* (*average*).—0.9 cm.
*Style color.*—90D.
*Stigma shape.*—Decurrent.
*Stigma color.*—90D.
*Ovary position.*—Superior.
*Ovary color.*—144B.

The invention claimed is:

1. A new and distinct cultivar of *Caryopteris* plant named 'WHITE SURPRISE' as described and illustrated herein.

* * * * *